(12) United States Patent
Fujii et al.

(10) Patent No.: US 7,385,048 B2
(45) Date of Patent: Jun. 10, 2008

(54) PROMOTERS AND UTILIZATION THEREOF

(75) Inventors: Toshio Fujii, Kanagawa (JP); Toshiya Ogawa, Kanagawa (JP); Masaharu Yoshioka, Kanagawa (JP); Kanji Mamiya, Tochigi (JP); Toshihiro Toguri, Tochigi (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 146 days.

(21) Appl. No.: 11/500,877

(22) Filed: Aug. 9, 2006

(65) Prior Publication Data

US 2006/0277623 A1    Dec. 7, 2006

Related U.S. Application Data

(62) Division of application No. 10/220,612, filed as application No. PCT/JP01/01376 on Feb. 23, 2001, now Pat. No. 7,115,420.

(30) Foreign Application Priority Data

Mar. 3, 2000    (JP)    ............... 2000-59276

(51) Int. Cl.
C12N 15/82    (2006.01)
(52) U.S. Cl. .................. 536/24.1; 435/320.1; 435/468
(58) Field of Classification Search ................... None
See application file for complete search history.

(56) References Cited

U.S. PATENT DOCUMENTS 5,097,025 A * 3/1992 Benfey et al. ............. 536/23.6
5,723,754 A    3/1998 Scott et al.

FOREIGN PATENT DOCUMENTS

| WO | WO 99/29880 A | 6/1999 |
| WO | WO 99/41393 A1 | 8/1999 |
| WO | WO 00/60061 A2 | 10/2000 |

OTHER PUBLICATIONS

Anderson, et al., "Human gene therapy," Nature, Apr. 30, 1998; 392(6679 Suppl); 25-30. Review.
Ellis et al., "Does the ocs-element occur as a functional component of the promoters of plant genes?" Plant J. Sep. 1993; 4(3):433-43.
Ha et al., "Cis-acting regulatory elements controlling temporal and organ-specific activity of nopaline synthase promoter," Nucleic Acid Research, Jan. 11, 1989; 17(1):215-23.
Hohn et al., "Methylation of coding region alone inhibits gene expression in plant protoplasts", Proc. Natl. Acad. Sci. USA vol. 93, pp. 8334-8339 (1996).
Kim et al., "A 20 nucleotide upstream element is essential for the nopaline synthase (nos) promoter activity," Plant Mol. Biol., Jan. 1994; 24(1): 105-17.
Matzke et al., "How and why do plants inactivate Homologous (Trans)genes?" Plant Physiol. 107, pp. 679-685 (1995).
Meyer et al., "Homology-dependent gene silencing in plants", Annu. Rev. Plant Physiol. Plant Mol. Biol. 47, pp. 23-48 (1996).
Meyer et al., "Evidence for cytosine methylation of non-symmetrical sequences in transgenic *Petunia hybrida*", the EMBO Journal vol. 13, No. 9, pp. 2084-2088 (1994).
Namba et al., "Expression of the gene encoding the coat of protein of cucumber mosaic virus (CMV) strain WL appears to provide protection to tobacco plants against infection by several differenct CMV strains," Gene (1991), vol. 107, No. 2, pp. 181-188.
Razin, "CpG methylation, chromatin structure and gene silencing—a three-way connection", The EMBO Journal vol. 17, No. 17, pp. 4905-4908 (1998).

* cited by examiner

*Primary Examiner*—Cynthia Collins
(74) *Attorney, Agent, or Firm*—Foley & Lardner LLP (57) ABSTRACT

The present invention relates to improved promoters and utilization thereof, in particular to promoters which are improved so as not to undergo methylation in the course of constructing transformants, and utilization thereof. According to the present invention, the expression efficiency of a structural gene can be enhanced even in a plant, e.g. *chrysanthemum*, which has weak expression of the structural gene by a cauliflower mosaic virus 35S promoter which as been considered a high expression promoter for plants.

6 Claims, 5 Drawing Sheets

Fig.1A

```
-263  AAGCTT-AAAAGGAAGGTGGCTCCTACAAATGCCATCATTGTGATAAAGG  -215
      ||| |||||||||||||||||||||||||||||||||||| |||||||
-263  TAG-TGGAAAAGGAAGGTGGCTCCTACAAATGCCATCATTGCGATAAAGG  -215

-214  AAAGGCTATCATTGAAGATGCCTCTACCTATAGTGGTCCCAAAGATGGAC  -165
      ||||||  ||| |||||||||||||  |  |||||||||||||||||||
-214  AAAGGCCATCGTTGAAGATGCCTCTGCCGACAGTGGTCCCAAAGATGGAC  -165

-164  CCCCACCCATGAGGAGCATGGTAGAAAAAGAAGATGTTCCAACCATGTCT  -115
      |||||||| |||||||||||| |||||||||||| |||||||||| |||
-164  CCCCACCCACGAGGAGCATCGTGGAAAAAGAAGACGTTCCAACCACGTCT  -115

-114  TCAAAGCAAGTGGATTGATGTGG-ATCCTCCAATGATGTCAAGG-ATGAT  -67
      |||||||||||||||||||||| |||  || ||| ||  ||| |||| 
-114  TCAAAGCAAGTGGATTGATGTGATATC-TCCACTGACGT-AAGGGATGAC  -67

-66   GTCA-AATCCCACTATCCTT-GCCAAGATC-TTCCTCTATATAAGGAAG  -20
      | || ||||||||||||||| ||  ||||| ||||| ||||||||||||
-66   G-CACAATCCCACTATCCTTCGC-AAGACCCTTCC-TCTATATAAGGAAG  -20

-19   TTCATTTCATTTGGAGAGG  -1
      ||||||||||||||||||
-19   TTCATTTCATTTGGAGAGA  -1
```

Fig.1B

```
-263  AAGCTT-AAAAGGAAGGTGGCTCCTACAAATGCCATCATTGTGATAAAGG  -215
      ||| |||||||||||||||||||||||||||||||||||| |||||||
-263  TAG-TGGAAAAGGAAGGTGGCTCCTACAAATGCCATCATTGCGATAAAGG  -215

-214  AAAGGCTATCATTGAAGATGCCTCTACCTATAGTGGTCCCAAAGATGGAC  -165
      ||||||  ||| |||||||||||||  |  |||||||||||||||||||
-214  AAAGGCCATCGTTGAAGATGCCTCTGCCGACAGTGGTCCCAAAGATGGAC  -165

-164  CCCCACCCATGAGGAGCATGGTAGAAAAAGAAGATGTTCCAACCATGTCT  -115
      |||||||| |||||||||||| |||||||||||| |||||||||| |||
-164  CCCCACCCACGAGGAGCATCGTGGAAAAAGAAGACGTTCCAACCACGTCT  -115

-114  TCAAAGCAAGTGGATTGATGTGG-ATCCTCCAATGACGTCAAGG-ATGAC  -67
      |||||||||||||||||||||| |||  || ||| || |||| ||||
-114  TCAAAGCAAGTGGATTGATGTGATATC-TCCACTGACGT-AAGGGATGAC  -67

-66   GTCA-AATCCCACTATCCTT-GCCAAGATC-TTCCTCTATATAAGGAAG  -20
      | || ||||||||||||||| ||  ||||| ||||| ||||||||||||
-66   G-CACAATCCCACTATCCTTCGC-AAGACCCTTCC-TCTATATAAGGAAG  -20

-19   TTCATTTCATTTGGAGAGG  -1
      ||||||||||||||||||
-19   TTCATTTCATTTGGAGAGA  -1
```

PROMOTERS AND UTILIZATION THEREOF

TECHNICAL FILED

The present invention relates to improved promoters and utilization thereof, in particular to promoters which are improved so as not to undergo methylation in the course of constructing transformants, and utilization thereof.

DISCLOSURE OF THE INVENTION

In constructing a desired transformant plant, one of the important elements is a high expression promoter. A promoter sequence is a main factor determining transcription level of a gene in plant cells, and in general use of a promoter sequence having a strong transcription activity enables the expression level of target foreign gene to be enhanced. Further, since it becomes remarkably easy to obtain a transformant plant by enhancing expression level of a maker gene, the high expression promoter is also important in expressing a drug resistant gene marker for producing a transformant plant.

Under this circumstance, there have been many reports on obtainment of a high expression promoter in a plant. Typical examples include a cauliflower mosaic virus (CaMV) 35S promoter, and promoters of an isopentenyl transferase (ipt) gene and a nopaline synthetase (nos) gene of *Agrobacterium*. Further, some cases have been observed where a high expression gene promoter obtained from a genome of a plant which is an object of a transformant host, and is utilized (Genschik et al., Gene, 148 (1994) 195-202). In recent years, it has been demonstrated that from among chimeric promoters in which a plurality of these promoters are combined, a promoter with remarkably increased promoter activity can be obtained. By way of example, Min Ni et al. demonstrated that by combining a promoter of an octopine synthetase (ocs) gene with a promoter of a mannopine (man) synthetase gene derived from *Agrobacterium*, a promoter showing high expression in tobacco could be obtained (Plant Journal, 7 (1995) 661-676).

However, even if these high expression promoters are used, a plant with a required level of expression of a foreign gene cannot necessarily be obtained in all kinds of plants. One of the reasons for this may be the existence of specificity based on difference of RNA polymerase existing in each plant cell. Further, as another reason, it is conjectured that a plant has a mechanism to suppress the expression of the foreign gene. Methylation of cytosine in genome DNA is considered to be a major factor involved in this gene inactivation or the mechanism for expression suppression (Meyer and Saedler, Annu. Rev. Plant Physiol. Plant Mol. Biol., 47 (1996) 23-48).

This methylation of cytosine is known to take place outstandingly in a double stranded DNA sequence wherein the nucleotide sequences of CG and CNG (N represents any nucleotide) form a palindrome structure (Matzke and Matzke, Plant Physiol. 107 (1995) 679-685). Methylation is also known to occur even in cytosine of other DNA sequences (Meyer et al., EMBO Journal, 13 (1994) 2084-2088). When cytosine is methylated, it is known that gene expression is suppressed in many organisms (Razin, EMBO Journal, 17 (1998) 4905-4908). In addition, because in a plant genome, the ratio of methylated cytosine is higher in comparison with other organisms, it has been reported that methylation is closely related to gene inactivation (Meyer and Saedler, Annu. Rev. Plant Physiol. Plant Mol. Biol., 47 (1996) 23-48). In particular, with respect to a cause for a phenomenon of suppressing the expression of a foreign gene introduced by gene manipulation etc., that is to say "gene silencing", inactivation by DNA methylation is assumed to be involved.

However, it has not been reported so far that controlling methylation of a promoter enhances gene expression. There has been only one report on a transient decline of gene expression by forcibly methylating in vitro a gene construct prepared by ligating a CaMV 35S promoter to a β-glucuronidase (Gus) gene (Hohn et al., Proc. Natl. Acad. Sci. USA, 93 (1996) 8334-8339). However, in the experiment of the above report, it was not verified which nucleotide sequence in vivo was subjected to methylation, and whether the result of that lead to decline of expression. Further, Hohn et al. observed that methylation of not only a promoter but also cytosine of a structural gene portion caused decline of expression of the Gus gene, and concluded that it was significant for high expression that the structural gene portion should not be subjected to modification with a methyl group. Thus, they seem rather negative toward the idea of high expression by using a demethylation promoter.

Accordingly, no specific method has been known for enhancing gene expression level by obviating methylation of a promoter. On top of that, in order to obtain a more highly expressing transformant host by avoiding methylation, it has not been known which CG or CNG sequence of a promoter portion or a DNA strand including a promoter portion should specifically be modified to what other nucleotides.

DISCLOSURE OF THE INVENTION

It is an object of the present invention to provide a promoter which activates the expression of a structural gene when the promoter is placed at 5' side of the structural gene. Further, it is another object of the present invention to provide a DNA strand comprising the promoter. Moreover, it is still another object of the present invention to provide a host which is transformed by the DNA strand and a method for high expression of a structural gene by use of the host.

The inventors, in view of the above-mentioned points, thought that a high expression promoter could be produced by modifying a palindrome DNA sequence consisting of CG and CNG in a double stranded DNA sequence of the promoter to other nucleotides free from CG and CNG sequences without loss of promoter activity and so as to be less likely to undergo methylation. Based on this idea, as a result of intensive studies, the inventors found that the expression level of the foreign gene in a *chrysanthemum* plant could significantly be enhanced by ligating a newly designed promoter to a constituent element such as a translation enhancer, a structural (reporter) gene, a translation termination codon and a terminator, and by transforming the *chrysanthemum* plant using the promoter. By this finding, the present invention has been accomplished.

Accordingly, the present invention provides a DNA represented by the following (a) or (b):

(a) a DNA comprising a nucleotide sequence consisting of the nucleotide sequence shown in SEQ ID NO:1 from nucleotide No. 7 to nucleotide No. 272; or (b) a DNA comprising a nucleotide sequence consisting of the nucleotide sequence shown in SEQ ID NO:1 from nucleotide No. 7 to nucleotide No. 272, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198 and 217 to 218, and the deleted, added or inserted sequence is free from any consecutive sequences represented by CG, CAG, CTG, CCG or CGG, and the DNA having promoter activity.

Further, the present invention provides a DNA represented by the following (c) or (d):

(c) a DNA comprising a nucleotide sequence consisting of the nucleotide sequence shown in SEQ ID NO:1; or (d) a DNA comprising a nucleotide sequence consisting of the nucleotide sequence shown in SEQ ID NO:1, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198 and 217 to 218, and the deleted, added or inserted sequence is free from any consecutive sequences represented by CG, CAG, CTG, CCG or CGG, and the DNA having promoter activity.

Furthermore, the present invention provides a DNA represented by the following (e) or (f):

(e) a DNA comprising a nucleotide sequence consisting of the nucleotide sequence shown in SEQ ID NO:2 from nucleotide No. 7 to nucleotide No. 272; or (f) a DNA comprising a nucleotide sequence consisting of the nucleotide sequence shown in SEQ ID NO:2 from nucleotide No. 7 to nucleotide No. 272, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 183 to 188, 195 to 200 and 217 to 218, and the deleted, added or inserted sequence is free from any consecutive sequences represented by CG, CAG, CTG, CCG or CGG (where nucleotide nos. 185 to 186 and 197 to 198 are each CG), and the DNA having promoter activity.

In addition, the present invention provides a DNA represented by the following (g) or (h):

(g) a DNA comprising a nucleotide sequence consisting of the nucleotide sequence shown in SEQ ID NO:2; or (h) a DNA comprising a nucleotide sequence consisting of the nucleotide sequence shown in SEQ ID NO:2, wherein one to several nucleotides are deleted, added and inserted at a site other than nucleotide nos. 41 to 42, 59 to 60, 73 to 75, 77 to 78, 80 to 82, 109 to 110, 119 to 120, 134 to 135, 145 to 146, 181 to 183, 183 to 188, 195 to 200 and 217 to 218, and the deleted, added or inserted sequence is free from any consecutive sequences represented by CG, CAG, CTG, CCG or CGG (where nucleotide nos. 185 to 186 and 197 to 198 are each CG), and the DNA having promoter activity.

Moreover, the present invention provides a DNA represented by the following (i) or (j):

(i) a DNA comprising a nucleotide sequence consisting of the nucleotide sequence shown in SEQ ID NO:3 from nucleotide No.7 to nucleotide No. 322; or (j) a DNA-comprising a nucleotide sequence consisting of the nucleotide sequence shown in SEQ ID NO:3 from nucleotide No. 7 to nucleotide No. 322, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248 and 267 to 268, and the deleted, added or inserted sequence is free from any consecutive sequences represented by CG, CAG, CTG, CCG or CGG, and the DNA having promoter activity.

Additionally, the present invention provides a DNA represented by the following (k) or (l):

(k) a DNA comprising a nucleotide sequence consisting of the nucleotide sequence shown in SEQ ID NO:3; or (l) a DNA comprising a nucleotide sequence consisting of the nucleotide sequence shown in SEQ ID NO:3, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248 and 267 to 268, and the deleted, added or inserted sequence is free from any consecutive sequences represented by CG, CAG, CTG, CCG or CGG, and the DNA having promoter activity.

Further, the present invention provides a DNA represented by the following (m) or (n):

(m) a DNA comprising a nucleotide sequence consisting of the nucleotide sequence shown in SEQ ID NO:4 from nucleotide No.7 to nucleotide No.422; or (n) a DNA comprising a nucleotide sequence consisting of the nucleotide sequence shown in SEQ ID NO:4 from nucleotide No. 7 to nucleotide No. 422, wherein one to several nucleotides are deleted, added or inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248, 267 to 268, 281 to 283, 285 to 286, 297 to 298, 317 to 318, 331 to 333, 335 to 336, 347 to 348 and 367 to 368, and the deleted, added or inserted sequence is free from any consecutive sequences represented by CG, CAG, CTG, CCG or CGG, and the DNA having promoter activity.

Furthermore, the prevent invention provides a DNA represented by the following (o) or (p):

(o) a DNA comprising a nucleotide sequence consisting of the nucleotide sequence shown in SEQ ID NO:4; or (p) a DNA comprising a nucleotide sequence consisting of the nucleotide sequence shown in SEQ ID NO:4, wherein one to several nucleotides are deleted, added and inserted at a site other than nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248, 267 to 268, 281 to 283, 285 to 286, 297 to 298, 317 to 318, 331 to 333, 335 to 336, 347 to 348 and 367 to 368, and the deleted, added or inserted sequence is free from any consecutive sequences represented by CG, CAG, CTG, CCG or CGG, and the DNA having promoter activity.

Moreover, the present invention provides a DNA strand comprising any of the above DNAs. Such a DNA strand preferably comprises a structural gene DNA and any of the above DNAs which is incorporated at 5' site of the structural gene DNA in a manner such that it is expressed. These DNA strands may include a constituent element selected from the group consisting of a translation enhancer, a translation termination codon, a terminator and combinations thereof. Further, the present invention provides a host which is transformed by the above DNA strand. The host is preferably a plant cell.

Furthermore, the present invention provides a method for expressing a structural gene in a plant which is characterized in that the host transformed by the above DNA strand is cultured or cultivated so as to enable expression of the structural gene. In this method, the structural gene may be a foreign gene. In addition, the present invention provides a method for producing a protein which is an expression product of a structural gene whose transcription is activated or whose expression is promoted by a DNA having promoter activity, using the host transformed by the above DNA strand.

Moreover, the present invention provides a transformant plant which is obtained by regeneration from a plant cell transformed by the above DNA strand.

Additionally, the present invention provides a DNA strand which comprises a selection marker gene DNA and any of the above DNAs which are incorporated at the 5' site of the selection marker gene DNA in a manner such that the selection marker gene is expressed. Further, the present invention provides a method for selecting a transformant host, which comprises the steps of transforming the host by the DNA strand, and culturing the obtained host under a condition in which the selection marker gene can be expressed and it can be identified whether or not the host expresses the selection marker gene. The host is preferably a plant cell.

This specification includes part or all of the contents as disclosed in the specification and/or drawings of Japanese Patent Application No. 2000-59276, which is a priority document of the present application.

DESCRIPTION OF SEQUENCE LISTS

SEQ ID NOS: 1 to 4: synthesized DNAs comprising promoter sequences
SEQ ID NOS: 5 to 24: primers

BRIEF DESCRIPTION OF THE DRAWINGS

FIGS. 1A and 1B show the comparison between promoters of the present invention: a DNA sequence of MF-48 (FIG. 1A) and a DNA sequence of MF-18 (FIG. 1B) (upper lines respectively), and a DNA sequence of a 35S promoter of pBI121 (lower lines).

BEST MODE FOR CARRYING OUT THE INVENTION (1) Promoter

A DNA of the present invention is a DNA comprising a nucleotide sequence represented by any of SEQ ID NOS: 1 to 4 or a part thereof having promoter activity. These DNAs are prepared by modifying some of nucleotides in the nucleotide sequences of a CaMV 35S promoter.

Thirteen CGs or CNGs exist 250 bp upstream from transcription initiation site of the CaMV 35S promoter, and it is estimated that these nucleotide sequences are methylated by CG methylation enzyme or CNG methylation enzyme, respectively. Therefore, a DNA in which these sequences are substituted by sequences which are not subjected to methylation, is one comprising a nucleotide sequence shown in SEQ ID NO: 1. In SEQ ID NO: 1, the portion having promoter activity is the portion from nucleotide nos. 7 to 272.

In addition, utilizing methylation-free property of the DNA (promoter) comprising the nucleotide sequence shown in SEQ ID NO: 1, a region of the promoter, which is called ocs region or as-1 region, comprising about 20 nucleotides (Ellis et al., Plant J., 4 (1993) 433-443; Lam et al., Proc. Natl. Acad. Sci. USA, 86 (1989) 7890-7894) can be further modified and this is considered particularly effective. Then, while retaining CG sequences in the ocs region, modification is carried out to form a palindrome structure of 6 nucleotides (GACGTC), thereby obtaining a DNA comprising a nucleotide sequence shown in SEQ ID NO: 2. The portion of SEQ ID NO: 2 having promoter activity is the portion from nucleotide nos. 7 to 272.

The comparison between the nucleotide sequences shown in SEQ ID NOS: 1 and 2 (upstream from transcription initiation site), and the sequence of the 35S promoter included in a vector pBI121 (manufactured by Clontech Company) which is the most commonly used in plant gene manipulation is shown in FIGS. 1A and 1B.

Moreover, as a modification concerning the ocs region, it is considered to conduct synthesis for repeating ocs region in the promoter, and this is thought to strengthen promoter activity. Thus, ocs region is repeated such that there are two ocs regions in the SEQ ID NO: 1, thereby obtaining a DNA comprising a nucleotide sequence shown in SEQ ID NO: 3. In SEQ ID NO: 3, a part of nucleotide nos. 7 to 322 has promoter activity. Further, in SEQ ID NO: 1, ocs regions is repeated such that there are four ocs regions, thereby obtaining a DNA comprising a nucleotide sequence shown in SEQ ID NO: 4. The portion of SEQ ID NO: 4 having promoter activity is the portion from nucleotide nos. 7 to 422.

The above DNAs of the present invention can be obtained by chemical synthesis in accordance with a method of nucleic acid biosynthesis.

Additionally, a DNA of the present invention includes a DNA (a variant) which comprises a nucleotide sequence wherein, relative to any of the above nucleotide sequences, one to several nucleotides are deleted, added or inserted, and which has promoter activity. Herein, the number of the deleted, added or inserted nucleotides is not particularly limited, but it is preferably one to several, more preferably one to three, and most preferably one. Moreover, the DNA of the present invention may include a DNA (a variant) which comprises a nucleotide sequence having 80% or more, preferably 90% or more, more preferably 94% or more, and most preferably 99% or more homology with the nucleotide sequence of any of the above DNAs, and which has promoter activity. Herein these homology values are calculated using default parameters (initial settings) by using a nucleotide sequence comparison program: DNASIS-mac v3.7.

Thus, the variants comprise the nucleotide sequences partially different from the nucleotide sequences shown in SEQ ID NOS: 1 to 4, but in this case the rearrangement sites from the above CaMV 35S promoter are required to be retained. In other words, in SEQ ID NO: 1, nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, and 217 to 218 are not varied. Likewise, in SEQ ID NO: 2, nucleotide nos. 41 to 42, 59 to 60, 73 to 75, 77 to 78, 80 to 82, 109 to 110, 119 to 120, 134 to 135, 145 to 146, 181 to 183, 183 to 188, 195 to 200, and 217 to 218 are not varied. Further, in SEQ ID NO: 3, nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248, and 267 to 268 are not varied. Furthermore, in SEQ ID NO: 4, nucleotide nos. 41 to 42, 59 to 60, 73 to 75, 77 to 78, 80 to 82, 109 to 110, 119 to 120, 134 to 135, 145 to 146, 181 to 183, 185 to 186, 197 to 198, 217 to 218, 231 to 233, 235 to 236, 247 to 248, 267 to 268, 281 to 283, 285 to 286, 297 to 298, 317 to 318, 331 to 333, 335 to 336, 347 to 348, and 367 to 368 are not varied.

Moreover, the nucleotide sequences of the above variants are required to be free from any consecutive sequences represented by CG, CAG, CTG, CCG or CGG, but the nucleotide nos. 185 to 186 and 197 to 198 in SEQ ID NO: 2 are each exceptionally CG.

As long as the DNAs comprising the nucleotide sequences shown in these SEQ ID NOS: 1 to 4 or the variants thereof have promoter activity, the activity level thereof is not particularly limited, but it is preferable to substantially retain promoter activity of the DNAs comprising the nucleotide sequences shown in SEQ ID NO: 1 to 4 or promoter activity of the parts thereof. Here "substantially retaining promoter activity" of these DNAs or the parts thereof means, in a practical example using promoter activity, to retain almost the same usable level of activity under the same condition as these DNAs and the parts thereof. Further, the promoter activity described herein is defined as an activity preferably in plant cells, more preferably in *chrysanthemum* plants, and most preferably in a *chrysanthemum* cultivar, Reagan (*Chrysanthemum morifolium* cv. Reagan or *Dendranthema grandiflorum* cv. Reagan).

It is obvious that these variants can be selected and prepared without any special difficulty by a person, as long as the person is skilled in the art, with reference to the nucleotide sequences shown in SEQ ID NOS: 1 to 4 in accordance with the descriptions in literature such as Molecular Cloning (edited by Sambrook et al. (1989) Cold Spring Harbor Lab. Press, New York). Further, a person skilled in the art can obtain and utilize the variants with respect to a technique for artificially replacing, deleting, inserting or adding one or more nucleotides from the nucleotide sequences relative to the nucleotide sequences (site-specific derivation of mutation) shown in the above-mentioned SEQ ID NOS: 1 to 4, in accordance with techniques described in Proc. Natl. Acad. Sci. USA 81(1984) 5662-5666, WO85/00817, Nature 316(1985) 601-605, Gene 34(1985) 315-323, Nucleic Acids Res. 13(1985) 4431-4442, Proc. Natl. Acad. Sci. USA 79(1982) 6409-6413, Science 224(1984) 1431-1433, etc.

It can be verified according to a method for promoter activity determination as described below, whether or not the above obtained variants have promoter activity, and further whether or not they substantially have promoter activity of any of the DNAs comprising the nucleotide sequences shown in SEQ ID NO: 1 to 4 or the parts thereof.

The promoter activity of the above variants can be calculated preferably by preparing a vector having various reporter gene, such as genes of β-glucuronidase (Gus), luciferase (Luc), chloramphenicol acetyltransferase (Cat), β-galactosidase (Gal), nopalin synthetase (nos), octopine synthetase (ocs) etc. ("Plant genetic transformation and gene expression; a laboratory manual", edited by Draper, J. et al., Blackwell Scientific Publication, 1988) ligated to the downstream region of the novel promoter; inserting the vector into plant cell genome with various transforming methods (described later) which are conventionally well known and commonly used; and measuring expression level of the reporter gene, but it is not limited to this method. As one example thereof, in the case where a reporter gene is Gus, promoter activity in host cells is determined in accordance with (i) a histochemical Gus stain method and/or (ii) a method using fluorescent substrate (both methods are in Plant Molecular Biology Manual, C2 (1994) 1-32 (Ed.) Gelvin and Schilperoort, Kluwer Academic Publishers).

Moreover, amounts of protein were measured in accordance with, for example, the Bradford method (Anal. Biochem. 72 (1976) 248-254), and Gus activity was converted to a value per amounts of protein (for example, calculated as pmoleMU/min/mg protein) for determination of promoter activity.

Exemplary host cells to be preferably used for the DNA of the present invention are cells of various plants such as monocotyledons including rice, MUGI (general name of wheat, barley, rye and oat), corn, onion, lily, orchid, etc. and dicotyledons including soy bean, rapeseed, tomato, potato, chrysanthemum, rose, carnation, petunia, gypsophila, cyclamen, etc. Particularly preferable examples include cells of a plant such as *chrysanthemum* which has high chromosomal polyploidy. The reason for that is that a plant is considered to methylate genes for inactivating homologous genes, and since plants with high polyploidy have many homologous genes it is expected that these genes will be inactivated by a strong methylation mechanism. (Leitch and Bennett, Trends in Plant Sci., 2 (1997) 470-476) In addition, because of a high CG content of the genome (Thomas and Sherratt, Biochem. J., 62 (1956) 1-4), cells of plants having target sequences of methylation reaction in abundance are also preferable candidates.

(2) DNA Strand

According to the present invention, there is provided a DNA strand comprising the DNA of the present invention. Such a DNA strand can be used for transcribing any gene, and for use thereof a desired gene is incorporated into the DNA strand in an expressible form. Such a gene is typically a structural gene. Accordingly, the present invention further provides a structural gene DNA and a DNA strand comprising the DNA of the present invention which is incorporated at the 5' site of the structural gene DNA in a manner so as to express the structural gene.

A specific example of the DNA strand according to the present invention may be, for example, where the DNA of the present invention is inserted as a part of constituent element in a plasmid or a phage DNA.

When incorporating the structural DNA gene into such a DNA strand, the DNA or the structural DNA of the present invention can be arranged to enable expression of the structural gene. Examples of the structural gene DNA include β-glucan elicitor receptor (Umemoto et al., Proc. Natl. Acad. Sci. USA 94 (1997) 1029-1034), pad (Sano et al., Biotechnol. 15 (1997) 1290-1294) and a DNA encoding 2-5Aase or RNaseL (Ogawa et al., Natl. Biotechnol. 14 (1996) 1566-1569), but it is not limited to these.

The DNA strand of the present invention may further include a constituent element such as a translation enhancer, a translation termination codon, a terminator, etc. As a translation enhancer, translation termination codon, and terminator, known ones can be used in a suitable combination. Examples of a virus-originated translation enhancer include sequences of tobacco mosaic virus, alfalfa mosaic virus RNA4, bromomosaic virus RNA3, potato virus X, tobacco etch virus, etc. (Gallie et al., Nuc. Acids Res., 15 (1987) 8693-8711) Further, examples of a plant-originated translation enhancer include sequences derived from soy bean β-1,3-glucanase (Glu) (Isao ISHIDA, Norihiko MISAWA, edited by Kodansha Scientific, "Saibo-kogaku-jikkenn-sousa-nyumon" (Introductory for operation in cell engineering experiments), Kodansha Ltd., p. 119, 1992), and sequences derived from ferredoxin affinity subunit (PsaDb) of tobacco (Yamamoto et al., J. Biol. Chem., 270 (1995) 12466-12470). Examples of the terminator include terminators of nos gene, ocs gene, etc. (Annu. Rev. Plant Physiol. Plant Mol. Biol., 44 (1993) 985-994, "Plant genetic transformation and gene expression; a laboratory manual" described before). Moreover, it has been reported that activity can be enhanced by identifying the 35S enhancer part as a transcription enhancer in a promoter and ligating a plurality of them to each other in series (Plant Cell, 1 (1989) 141-150). This part can be used as a part of the DNA strand. These various constituent elements are preferably incorporated into the DNA strand in a form so as to function in accordance with their characters. A person skilled in the art can appropriately conduct such a manipulation.

The DNA (promoter) of the present invention includes a translation enhancer derived from Glu gene of soy bean after transcription initiation site (described as after nucleotide nos. 279 in SEQ ID NOS: 1 and 2, after nos. 329 in SEQ ID NO: 3, or after nos. 429 in SEQ ID NO: 4). Although this sequence is not directly related in transcriptional promotion due to its being methylation-free, it can further promote expression of a target gene. The translation enhancer is not limited to the one used in the present invention which is derived from Glu gene of soy bean, but the same effect can be expected even where it is replaced with an other translation enhancer such as the above which have been so far reported. Moreover, as with the present invention, the CG sequence of this translation enhancer can be replaced with other nucleotides. In addition, when the other translation enhancer has a CNG sequence other than a CG sequence, the CNG sequence can be replaced with other nucleotides in the same manner as with the CG sequence. A person skilled in the art can appropriately conduct such a modification.

The above DNA strand can easily be prepared by a person skilled in the art using a method which is commonly used in the field of gene engineering. Further, the DNA strand of the present invention is not limited to an artificial construct, and as long as it has a structure such as the above, it may be isolated from a natural source. The DNA strand can be obtained by synthesis according to a well-known and commonly used method of nucleic acid biosynthesis.

(3) Transformation

The DNA strand comprising the DNA having promoter activity of the present invention enables a host to be transformed, and the obtained transformant is cultured or cultivated, thereby allowing induction of expression of the structural gene, or expression of the structural gene with high efficiency. The structural gene may be a foreign gene.

The chain of the present invention after the transformation can be present in microorganisms (especially bacteria), phage particles or plants in a form of incorporation into plasmids, phages or genome DNA. Here typical examples of the bacteria include, but are not limited to, *Escherichia coli*, and *Agrobacterium*, etc.

In a preferable example of the present invention, the DNA strand of the present invention exists in plants in a form such that the DNA (promoter) of the present invention, the translation enhancer, the structural gene DNA, the translation termination codon, the terminator, etc. are integrally ligated and incorporated into a genome so that the structural gene which attempts to express a protein can be stably expressed in plants.

Preferable examples of the host include cells of monocotyledons such as rice, MUGI (general name of wheat, barley, rye and oat), corn, onion, lily, orchid, etc. and dicotyledons such as soy bean, rapeseed, tomato, potato, *chrysanthemum*, rose, carnation, petunia, gypsophila, cyclamen, etc., and in particular preferable examples are cells of plants such as *chrysanthemum*, etc. having a high chromosomal polyploidy. In addition, exemplary plant materials include growing points, shoot primordia, meristems, leaf pieces, stem pieces, root pieces, tuber pieces, petiole pieces, protoplast, calli, anthers, pollen, pollen tubes, peduncle pieces, scape pieces, petals, sepal pieces, etc.

As a biological method for introducing a foreign gene into the host, various methods which have already been reported and established can be used as appropriate. Preferable examples thereof include a method wherein Ti plasmid, Ri plasmid, etc. of virus or *Agrobacterium* are used as a vector, physical methods for introducing a gene with electroporation, polyethylene glycol, particle gun, micro-injection ("Plant genetic transformation and gene expression; a laboratory manual" described before), silicon nitride whisker, silicon carbide whisker (Euphytica 85 (1995) 75-80, In Vitro Cell. Dev. Biol. 31 (1995) 101-104, Plant Science 132 (1998) 31-43), and the like. A person skilled in the art can appropriately select and utilize a method of introduction.

Furthermore, a transformant plant which expresses the introduced gene in its cells can be prepared by regenerating the plant cells which have been transformed with the DNA strand of the present invention. This manipulation can easily be carried out by a person skilled in the art with a generally known method of regenerating plant cells to plants. Regarding regeneration of plant cells to plants, see literature, for example "SHOKUBUTU-SAIBOU BAIYOU MANUAL (Manual for Plant Cell Cultivation) (edited by Yasuyuki Yamada, Kodansha Scientific, 1984).

When an expression product of a gene which has been expression-induced or highly expressed, is desired for use as an isolated product, it can be isolated and purified from the culture according to an appropriate method depending on the expression product. The expression product of the target structural gene can be highly expressed by culturing such a host when the growth of a host cell and further properties of the cell are altered with the existence of the expression product, or by cultivating such a plant when the host is a dedifferentiated plant.

Moreover, the high expression promoter disclosed in the present invention permits remarkable enhancement of the efficiency of plant transformation by using a DNA strand expressing a selection marker of e.g. kanamycin resistant (e.g. NPTII) gene. This can be accomplished by using a selection marker gene DNA and a DNA strand comprising any of the above DNAs which is incorporated at the 5' site of the selection marker gene DNA in a form so as to express the selection marker gene. A specific procedure therefore is not particularly limited, but the procedure can be accomplished by e.g. transforming a host with the DNA strand, and culturing the obtained host under the conditions where the selection marker gene can be expressed, and whether or not the host expresses the selection marker gene can be determined. The host may be other than plant cells, so it is not particularly limited, but it is preferably a plant cell. Herein any selection marker gene can be used, so it is not particularly limited, but it is preferably a drug-resistant gene, e.g. NPTII gene (kanamycin resistant gene), Hyg$^r$ gene (hygromycin resistant gene), is usable. In this case, the condition for determining whether or not the host can express the selection marker gene, is attained by culturing it with a medium containing a drug to which the gene is resistant. A drug to be used may be kanamycin (Km) when NPTII gene is used as a selection marker gene, but it is not limited thereto, and G418 or paromomycin may be optionally selected for use. Further, the same effect can be expected when a DNA strand expressing e.g. a selection marker of hygromycin resistant (e.g. Hyg$^r$) gene is used. A drug used in this case may be hygromycin.

In this case also, as a method for obtaining a transformed plant by introducing the DNA strand into the host cells, any of the methods mentioned above can be used. Confirmation of the expression of the plant, when e.g. a reporter gene is Gus, can be carried out by the above (i) histochemical Gus stain method and/or (ii) a method using fluorescent substrates (Plant Molecular biology Manual, C2 (1994) 1-32, described before) etc.

In general, during cell differentiation, it is known that gene inactivation occurs by methylation. The promoter disclosed in the present invention is expected to cause high expression of a target gene not only in undifferentiated plant cells such as callus at transformation, but also in a plant.

INDUSTRIAL APPLICABILITY

According to the present invention, expression efficiency can be enhanced in a plant which shows weak expression of a structural gene by cauliflower mosaic virus 35S promoter conventionally regarded as a high expression promoter for plants, e.g. *chrysanthemum*.

EXAMPLES

The present invention will hereinafter be described with reference to the following Examples, but it is not limited thereto.

Example 1

Preparation of a Methylation Free Promoter

Thirteen CGs or CNGs exist 250 bp upstream from the mRNA (transcription) initiation site of a CaMV 35S promoter, and it is conjectured that these nucleotide sequences are subjected to methylation in plants by CG methylase and CNG methylase respectively. Accordingly, a DNA was synthesized in its entirety, by substituting these sequences by sequences which are not subjected to methylation. (MF-48: SEQ ID NO:1) Further, with respect to ocs region which is considered to have large influence especially on transcriptional activity, while CG sequences therein were retained, a DNA was prepared by modification so as to have a palindrome structure of 6 nucleotides (GACGTC). (MF-18: SEQ ID NO:2) A comparison between the sequences (upstream from the transcription initiation site) of MF-48 and MF-18 and the sequence of a 35S promoter included in a vector pBI121 which is usually most often used for plant gene manipulation, is shown in FIGS. 1A and 1B. In FIGS. 1A and 1B, the underlined parts indicate CG and CNG sequences which are said to be targets for methylation.

Besides the above, a gene (plasmid name is pSan9: Proc. Natl. Acad. Sci. USA, 93 (1996) 8334-8339, described before) having methylation target sites of 35S promoter which has been modified was transferred from Dr. Hohn of Friedrich Miescher-Institut (Switzerland). This gene was composed of a promoter portion of about 250 nucleotide pairs upstream of mRNA transcription initiation site, a 5' non-translation sequence of about 50 nucleotide pairs of a CaMV 35S gene downstream thereof (hereinafter the combination of the promoter portion and the 5' non-translation sequence is referred to as "MF-28"), and a Gus gene expression cassette further downstream thereof comprising a Gus structural (reporter) gene and a 35S terminator.

Example 2

Preparation of a Vector Having a Methylation Free Promoter

In order to confirm the effect of the thus prepared MF-48, MF-18 and MF-28 in a transformed plant, expression vectors were constructed. The following expression vectors were all composed of expression units of a Gus gene and an NPTII gene within a region flanked by border sequences so that the transcription directions thereof were in opposition. For these expression cassettes, a binary type vector, pKT11 which was amplifiable with *Agrobacterium* and *Escherichia coli*, was used as a basic vector, and the promoters of the Gus gene and NPTII gene was replaced, thereby constructing pKT81, pKT83 and pMF-28.

The binary type vector pKT11 was a vector composed of a XhoI-EcoRI portion about 250 bp which was an RB region of *Agrobacterium* A281, an HindIII-EcoRI portion about 3.5 kbp (ligating from 5' side in order of a CaMV 35S promoter, a translation enhancer of tobacco PsaDb, the Gus gene comprising an intron of a ricinus catalase gene and a nos gene terminator) which was an expression unit portion of the Gus gene, a HindIII-KpnI portion about 1.7 kbp (terminators of NPTII gene and nos gene which function in a plant driven by a nos gene promoter) which was an expression unit portion of the NPTII gene, and a KpnI-XhoI portion about 5.5 kbp which was a portion having a left border region derived from pBI121 and a replication origin amplifiable with *Agrobacterium* and *E. coli*. Further, it is a vector in which Gus gene is expressed by a promoter to which a translation enhancer of a soybean derived Glu gene is ligated (FIG. 2D).

Figure 2:
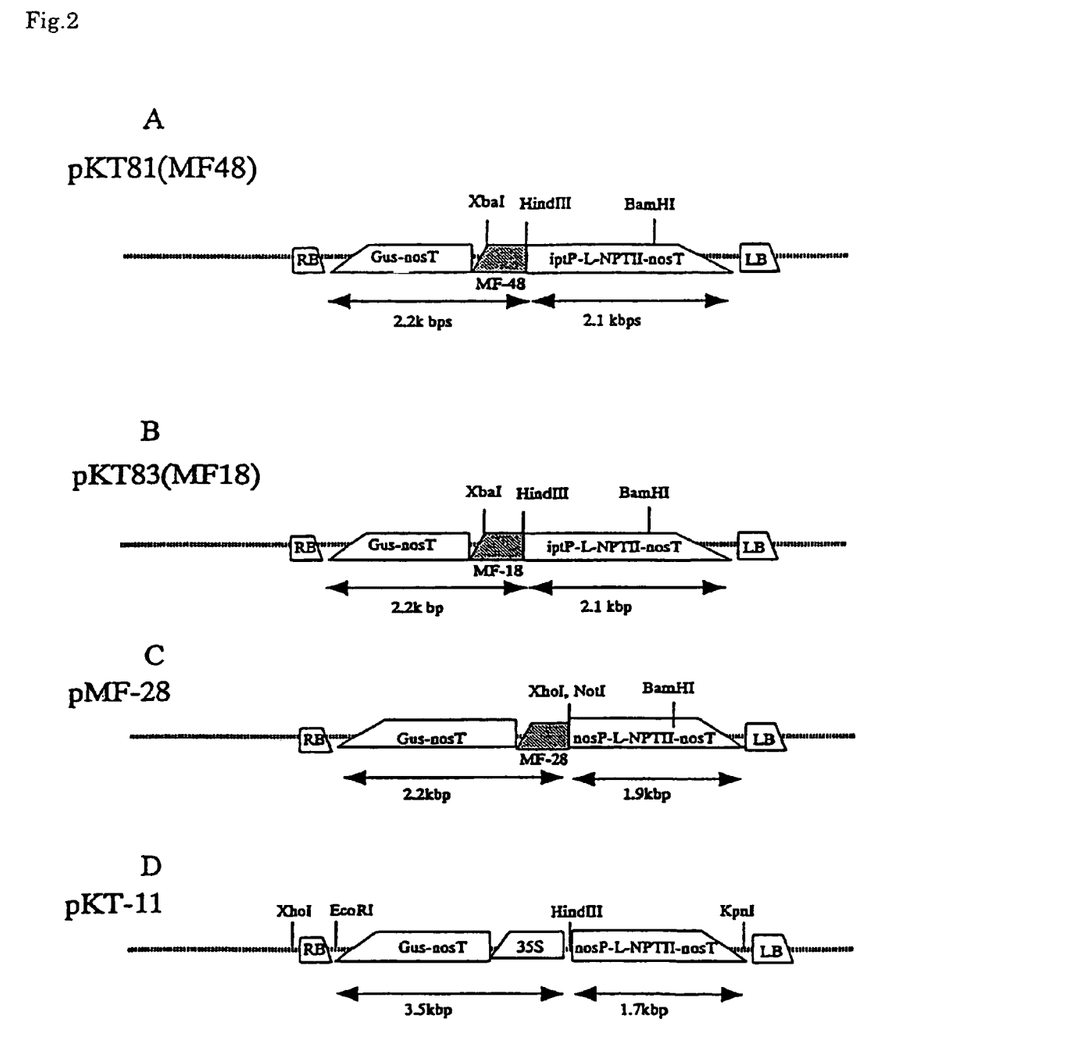
FIG. 2 illustrates a portion of structures of plasmids pKT81(A), pKT83(B), pMF-28(C) and pKT11(D).

The DNA fragments (promoter) prepared in Example 1 were purified by agarose gel, and the 35S promoter region (HindIII-XbaI) of the plasmid pKT11 was substituted, thereby preparing plasmids pKT81 and pKT83 (FIG. 2).

Each of pKT81 and pKT83 has a translation enhancer of soybean derived Glu gene derived from soybean, which is ligated downstream of MF-48 and MF-18 respectively, for the purpose of enhancing translation efficiency, and further downstream has an expression unit in which the Gus gene which was a reporter gene and the nos gene terminator are ligated. Simultaneously, each of them includes a expression unit in which an ipt gene promoter, a translation enhancer of Glu gene derived from soybean, an NPTII gene and an nos gene terminator are ligated.

In pMF-28, the entire Gus gene expression cassette of pSan9 was exchanged with Gus expression cassette of pKT11.

Restriction enzyme maps of vectors pKT81, pKT83 and pMF-28 which express Gus gene by promoters of MF-48 and MF-18, and MF-28 are shown in FIGS. 2A, B and C, and pKT11 to be used as a basal vector is shown in FIG. 2D.

Figure 3:
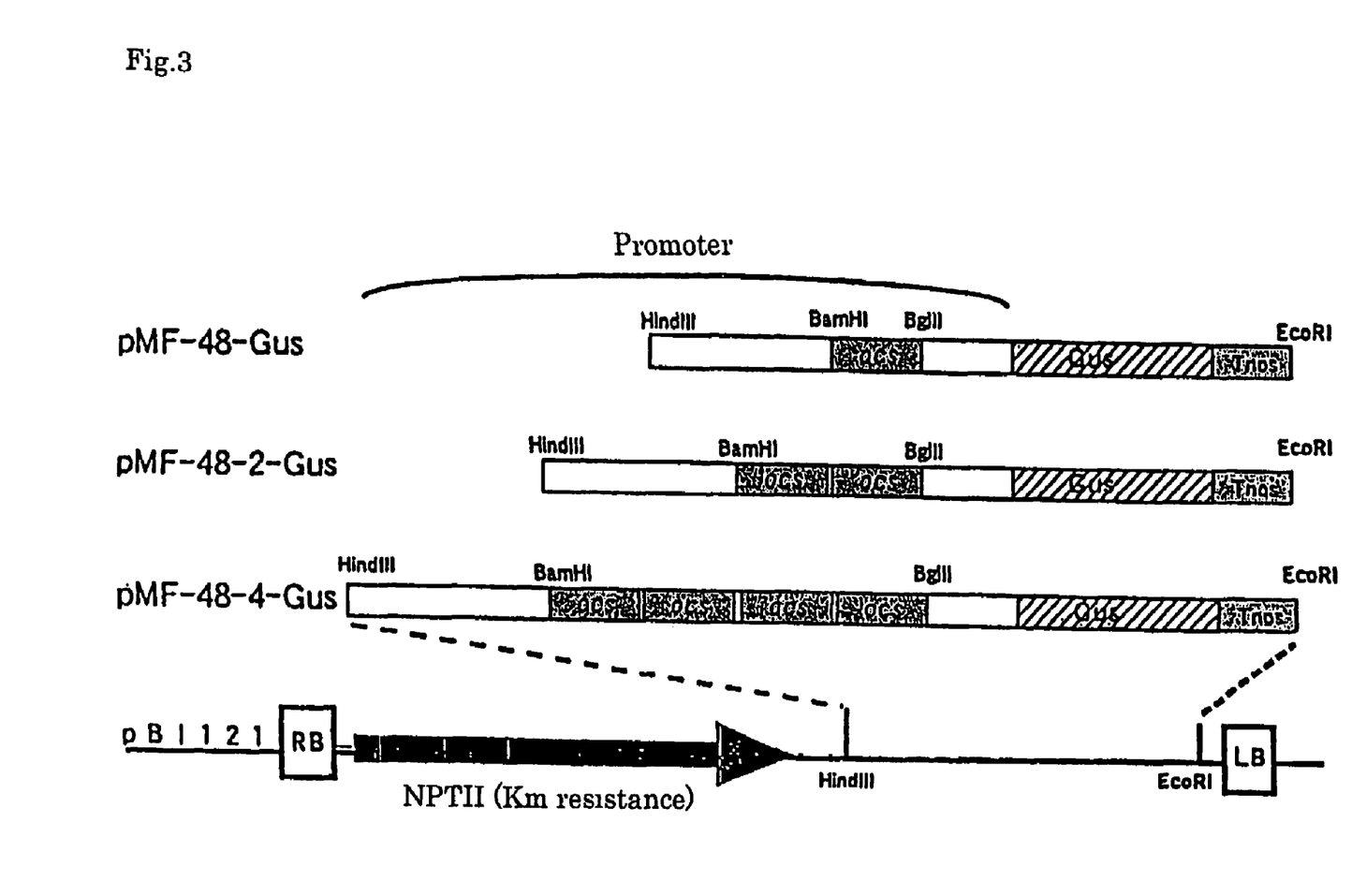
FIG. 3 illustrates a plasmid pMF-48-Gus, and its derivatives pMF-48-2 and pMF-48-4.

In addition, in order to prepare a promoter having increased ocs regions, the sequence between excision sites of each restriction enzyme BamHI and BglII, which is a region including ocs element of MF-48 promoter, was inserted into the fragment prepared by excising the promoter with BamHI, and there were prepared a promoter (MF-48-2: SEQ ID NO:3) having two copies of this sequence aligned in series in the same direction and a promoter (MF-48-4: SEQ ID NO:4) having four copies of this sequence aligned in series in the same direction. (FIG. 3)

Example 3

Preparation of *Chrysanthemum* Callus which Expresses Gus Gene

Vectors pKT81 and pKT83 which express Gus gene by promoters of MF-48 and MF-18, and a vector pKT11 as a control were each introduced by electroporation into *Agrobacterium tumefaciens* LBA 4404 strain, the obtained strain was inoculated in 3 ml of YEB-Km medium, and it was cultured for 16 hours at 28° C. in the dark. Thereafter, strain cells were collected by centrifugation, and suspended in 10 ml of the following infected medium, preparing the infected solution. The compositions of YEB-KM medium and the infected medium are as follows.

YEB-Km medium; 5 g/l beef extract, 1 g/l yeast extract, 5 g/l peptone, 5 g/l sucrose, 2 mM magnesium sulfate (pH 7.2), and 50 mg/l kanamycin Infected medium; inorganic salts and vitamins of ½ concentration of MS (Murashige & Skoog, Physiol. Plant., 15 (1962) 473-497) medium, 15 g/l sucrose, 10 g/l glucose, and 10 mM MES (pH 5.4)

Leaves from a sterile plant of Reagan (*Chrysanthemum morifolium* cv. Reagan or *Dendranthema grandiflorum* cv. Reagan), a cultivar of *chrysanthemum*, were cut into leaf pieces of 5 to 7 mm square, and the pieces were each dipped for 10 minutes into *Agrobacterium* infected solutions into which each of vectors pKT11, pKT81 and pKT83 was introduced. After wiping off any excess of the infected solution with a paper filter, the leaf pieces were transferred to the following co-cultivation medium and cultivated at 25° C. in the dark. After three-day cultivation, the leaf pieces were transferred to the following selection medium for three-week cultivation, thereby obtaining Km-resistant calli. Cultivation in the selection medium was conducted with conditions of 16-hour lighting (light density of 32 µE/m$^2$s)/8-hour non-lighting at 25° C. Four leaf pieces containing the obtained Km resistant callus for each vector, in total 12 leaf pieces, were used for Gus activity determination in order to confirm Gus gene expression.

Co-cultivation medium; inorganic salts and vitamins of MS medium, 30 g/l sucrose, 1 mg/l naphthalenacetic acid, 2 mg/l benzyladenine, 8 g/l agar, 5 mM MES (pH 5.8), and 200 µM acetosyringone Selection medium; inorganic salts and vitamins of MS medium, 30 g/l sucrose, 1 mg/l naphthalenacetic acid, 2 mg/l benzyladenine, 8 g/l agar, 5 mM MES (pH 5.8), 25 mg/l kanamycin, and 300 mg/l cefotaxime The leaf piece was transferred to 200 µl of a reaction solution (100 mM sodium phosphate buffer solution (pH 7.0), 1 mM EDTA, 0.1% Triton X-100, 1 mM dithiothreitol (DTT)) for determination of enzyme activity, and fully crushed while ice-cooling. The obtained suspension was centrifuged to collect a supernatant, and the supernatant was used as crude enzyme solution. The Gus activity determination was conducted in accordance with the published report (Plant Molecular Biology Manual, C2 (1994) 1-32, described before). Namely, 5 µl of the crude enzyme solution and 50 µl of 2.8 mg/ml 4-methylumbelliferyl-β-D-glucuronide as a substrate were added to 145 µl of the reaction solution, and the generated fluorescence was measured. The measurement of amounts of protein was conducted using Protein Assay Kit II of Bio-Rad Laboratories, and Gus activity per amounts of protein were determined. The following Table 1 shows Gus activity of calli which were transformed by pKT11, pKT81 and pKT83 respectively. Since the calli transformed by pKT81 and pKT83 exhibited about 4 to 5 times higher Gus activity than the callus transformed by pKT11, it was confirmed that methylation-free promoters: MF-48 and MF-18 have high expression ability.

TABLE 1

Expression of β-glucuronidase gene in *chrysanthemum callus* by various promoters

| Vector (Promoter) | β-glucuronidase (Gus) activity (pmole/min./mg protein) |
|---|---|
| pKT11(35S) | 4.43 |
| pKT81(MF-48) | 23.69 |
| pKT83(MF-18) | 15.71 |

With respect to MF-48-2 and MF-48-4, vectors were prepared by replacing 35S promoters of pBI121, and in the same manner as above, using chrysanthemum leaves as material, transformation was conducted, thereby obtaining Km resistant calli. Using these calli, in accordance with the method described in Plant Molecular Biology Manual, C2 (1994) 1-32 (described before), a tissue stain process was conducted with Gus activity. Color development was not observed with pBI121, but in contrast remarkably strong blue color development was observed with MF-48-2 and MF-48-4. In other words, with regard to qualitative expression strength, pBI121 was negative (−), but in contrast MF-48-2 and MF-48-4 were positive (+) to (++).

Example 4

Preparation of a *Chrysanthemum* Plant Which Expresses Gus Gene

In plant transformation, it is often observed that even though a promoter can be highly expressed in undifferentiated cells like callus, that promoter can be highly expressed in only a few cells of grown plants. As one of the reasons for this phenomenon, it is thought that gene methylation is stimulated to suppress unnecessary gene expression when the plant cells differentiate. In view of the foregoing, we thought that a methylation-free promoter disclosed in the present invention can be highly expressed in grown plants, too, and thus we examined this.

*Agrobacterium tumefaciens* LBA 4404 strains each containing pKT81, pKT83, and pMF-28 were transformed in accordance with the method of Example 3, and Km resistant calli were obtained. From the obtained calli, plants were regenerated on MS medium containing Km (regeneration medium; the composition was the same as the selection medium of Example 3). Further, for facilitating rooting, the regenerated plants were grown on a rooting-facilitating medium wherein plant growth regulating substances (naphthalenacetic acid, benzyladenine) were removed from the regeneration medium.

From the grown plants, plants containing an NPTII gene as a foreign gene were detected by conducting PCR, and it was confirmed that the thus-obtained redifferentiated plants were transformants. Here as a primer for specific amplification of an NPTII gene-specific sequence, the sequences of TAAAGCACGAGGAAGCGGT (SEQ ID NO:5) and GCA-CAACAGACAATCGGCT (SEQ ID NO:6) were used. The reaction conditions for PCR were heating at 94° C. for 5 minutes; 30 cycles of 30 seconds at 94° C., 1 minute at 55° C., and 1 minute at 72° C.; and thereafter a reaction at 72°

C. for 10 minutes. In this reaction, ExTaq polymelase (manufactured by Takara Shuzo Co., Ltd.) was used as an enzyme.

Figure 4:
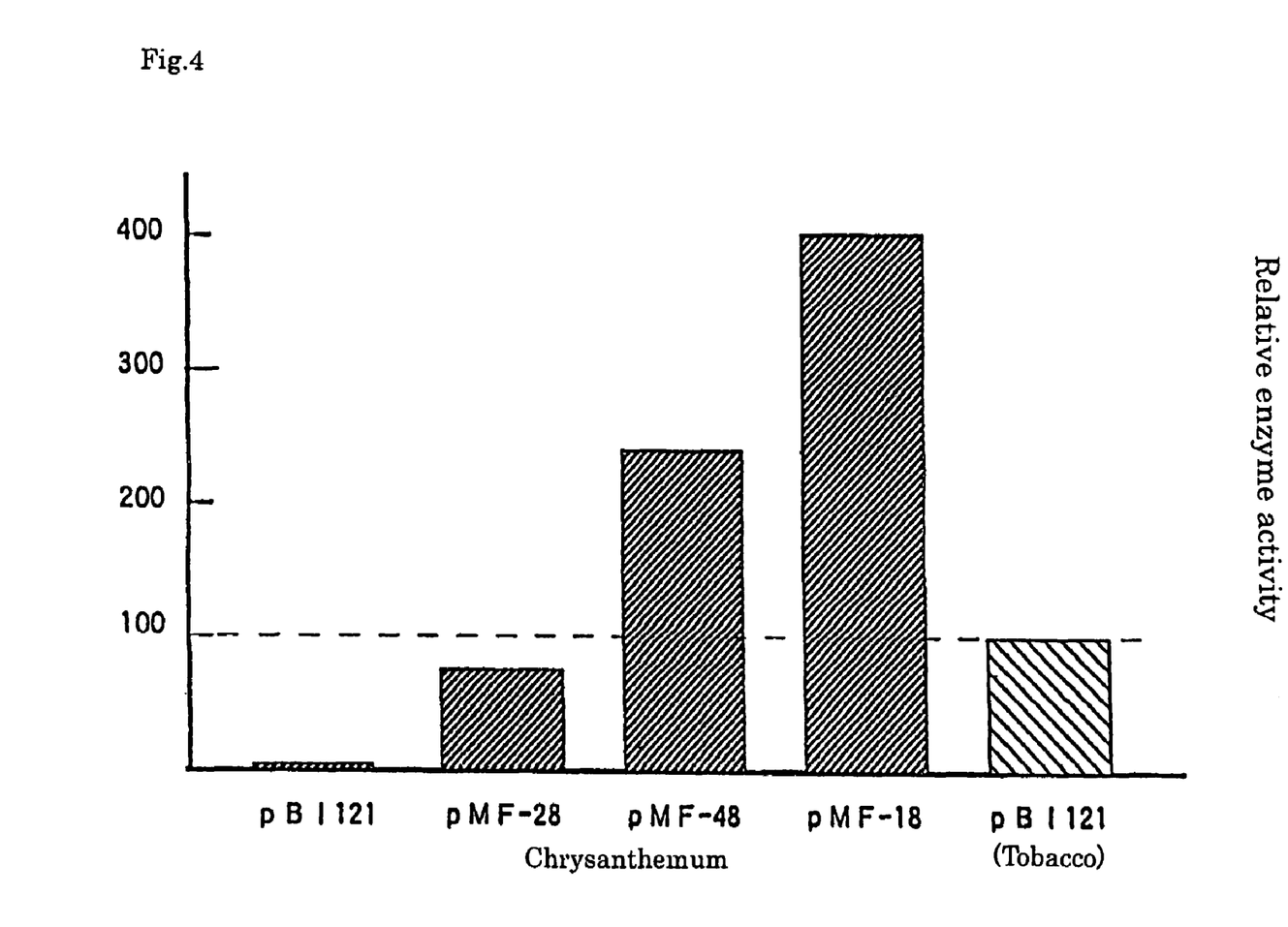
FIG. 4 shows relative values of averages (among 10 plants or more) of expression level of a Gus gene in *chrysanthemum* leaves transformed by 4 kinds of vectors, based on expression level of the Gus gene in recombinant tobacco transformed by pBI121 as comparison.

With respect to 3 leaves of each of these plants and 10 plants per each gene, the activity was determined in the same manner as Km resistant callus, and mean values of the determined activity are shown in FIG. 4. As a comparison, in accordance with the transformation method of Example 3, the experiments for introducing pBI121 into *chrysanthemum* and tobacco (variety: Xanthi) were conducted. Further, leaves of *chrysanthemum* transformants each having pKT81 (MF-48), pKT83(MF-18), and pMF-28(MF-28) introduced thereinto, were examined for measuring expression level of the Gus gene by a plant, and the results thereof are shown by a histogram in FIG. 5.

Figure 5:
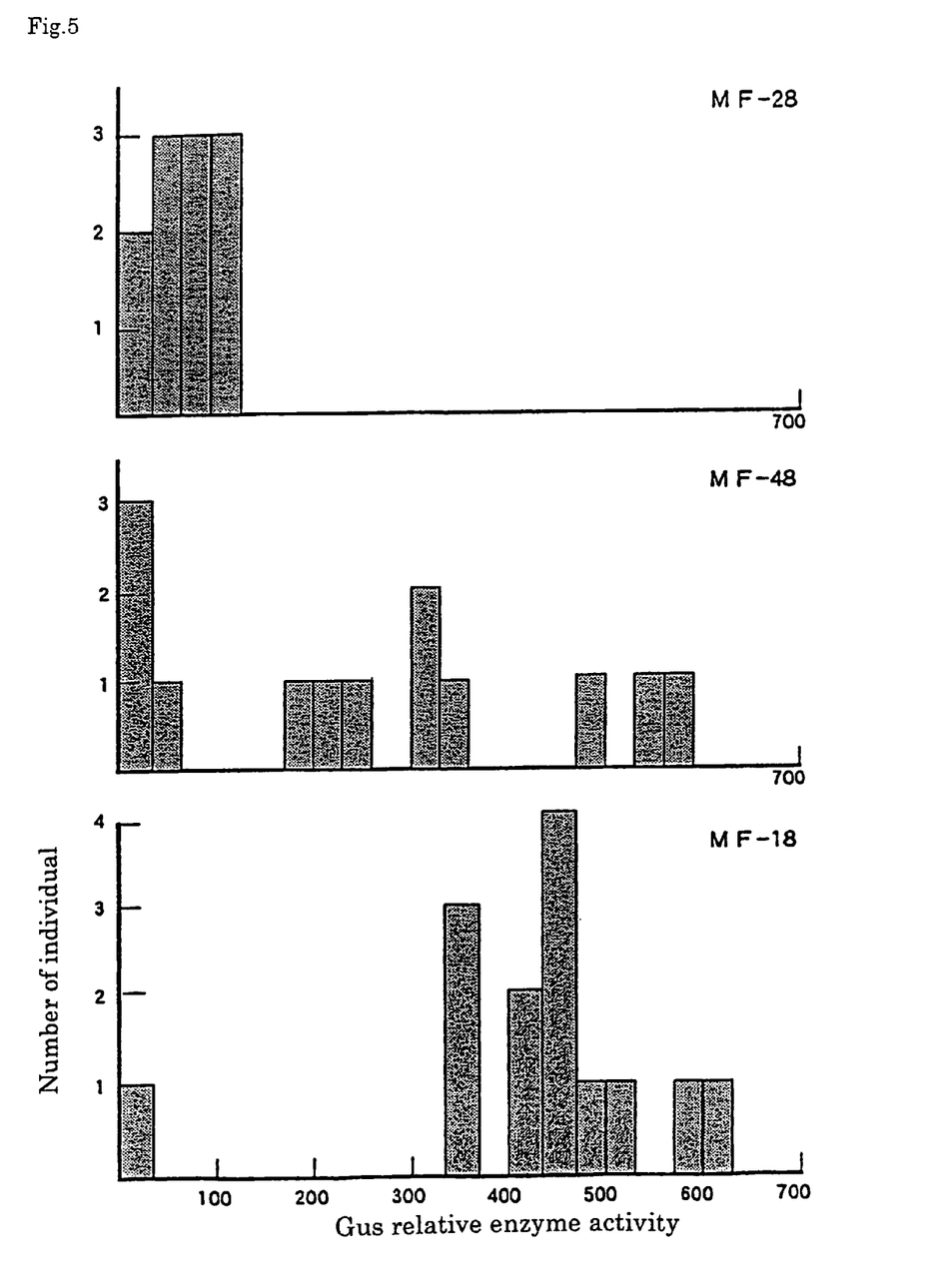
FIG. 5 shows distribution by plant of relative values (recombinant tobacco transformed by pBI121 was used as comparison) of expression level of the Gus gene in *chrysanthemum* leaves transformed by 3 kinds of vectors.

According to the results, it was observed that *chrysanthemums* having pKT81(MF-48), pKT83(MF-18), or pMF-28(MF-28) introduced thereinto each exhibited higher expression of the Gus gene than one having pBI121. However, the expression level of pMF-28 did not reach the expression level in tobacco which is well known as example of a high expression promoter. Nevertheless, surprisingly, pKT81 and pKT83 exhibited much higher expression level than pBI121(35S) in tobacco. Then, when pKT81(MF-48) and pKT83(MF-18) were compared with each other, pKT83 (MF-18) plants tended to exhibit higher expression of the Gus gene. (FIG. 4) In addition, the expression level in *chrysanthemum* by a plant was studied. For example, plants which exhibited more than three times the expression level of the Gus gene were limited to MF-48 and MF-18. As a whole, the number of plants exhibiting high expression was likely to be larger in the case of MF-18, compared with MF-48. (FIG. 5)

Example 5

Analysis of Foreign Gene Methylation in Transformed *Chrysanthemum*

In order to understand how the introduced gene is methylated in vivo, the location of methylated cytosine in the introduced gene sequence was determined. The analytical method to be used was cytosine deamination PCR method of Meyer et al. (EMBO Journal, 13 (1994) 2084-2088). An outline of the method is that firstly a DNA was extracted by CTAB from transformed *chrysanthemum* obtained in Example 4 and excised by a restriction enzyme EcoRI, suspended in a conversion buffer (3M Na-bissulfate, 0.5 mM hydroquinone, pH 5.3), and reacted at 50° C. for 20 hours in a nitrogen gas phase. After desalting by dialysis, DNA was alkali-denatured with 0.3N NaOH, and then precipitated by ethanol for collection. Next, using DNA primers designed to flank nucleotide sequence-determining site, PCR reaction was conducted. The PCR primers used herein are shown as follows.

<primer for analysis of 35S region methylation>

```
first PCR
35S-8:
GAATGTTAATTTATAGATGGTTAGAGAGGTTTATGT (SEQ ID NO:7)
AGTAGG 35S-8
CCATATTCTCTCCAAATAAAATAAAC             (SEQ ID NO:8)

second PCR
35S-9:
AGTAATAATTTTAGGAAATTAAATATTTTTTAAGA    (SEQ ID NO:9)
AGG 35S-14:
TATTCTCTCCAAATAAAATAAACTTC             (SEQ ID NO:10)
```

<primer for analysis of 35S complementary chain methylation>

```
first PCR
35S-C-1:
CTATTCCAATATAAACAATTCAAAACTTAC         (SEQ ID NO:11)

35S-C-4:
TGAAATGAATTTTTTTATATAGAGGAAGGGTTTTGT   (SEQ ID NO:12)
G second PCR
35S-C-2:
CAACATAATAAAACACAACACACTTATCTAC        (SEQ ID NO:13)

35S-C-3:
ATGAATTTTTTTATATAGAGGAAGGGTTTTGTGAA    (SEQ ID NO:14)
G
```

<primer for analysis of GUS gene methylation>

```
first PCR
35S-16:
GAAGAAATTTTTGTTAATATGGTGGAGTATGATATG   (SEQ ID NO:15)

TO-100:
CCAATCAACAAACACATAATTACAATCTTACACAAC   (SEQ ID NO:16)
ATACATC second PCR
35S-17:
GGGATGATGTATAATTTTATTATTTTTTGTAAGA     (SEQ ID NO:17)

TO-101
CATAACATCAACTTCAAATAACATATAACCACCCTA   (SEQ ID NO:18)
ATAC
```

<primer for analysis of Pac1 gene methylation>

```
first PCR
35S-16:
GAAGAAATTTTTGTTAATATGGTGGAGTATGATATG   (SEQ ID NO:15)

pac1-7:
CTTCAATAACAAATTCATTTTAACAATCATACC      (SEQ ID NO:19)

second PCR
35S-17:
GGGATGATGTATAATTTTATTATTTTTTGTAAGA     (SEQ ID NO:17)

pac1-8:
ACAAATTCATTTTAACAATCATACCTTAACT        (SEQ ID NO:20)
```

<primer for analysis of MF methylation>

```
first PCR
TO-103:
GAGGATTTAAAAGGAAGGTGGTTTTTATAAATGTTA   (SEQ ID NO:21)
TTATTG TO-105
CCACAATTTTCACAATCCAAACTAAATACCCACAAA   (SEQ ID NO:22)
CC:
GUS gene 5' region
```

-continued

```
second PCR
TO-104:
GGATTTAAAAGGAAGGTGGTTTTTATAAATGTTATT (SEQ ID NO:23)
ATTGTG TO-106:
CAATTTTCACAATCCAAACTAAATACCCACAAACCA (SEQ ID NO:24)
TC:
GUS gene 5' region
```

The reaction conditions for all the above PCR were initial heating at 94° C. for 5 minutes; 30 cycles of 30 seconds at 94° C., 1 minute at 65° C., and 1 minute at 72° C., followed by a reaction at 72° C. for 10 minutes. Secondly, using 1 μl of the firstly obtained PCR product, after carrying out heating at 94° C. for 5 minutes, a cycle of 30 seconds at 94° C., 1 minute at 60° C., and 1 minute at 72° C. was repeated 30 times. Finally a reaction at 72° C. for 10 minutes was carried out.

In this reaction, ExTaq polymelase (manufactured by Takara Shuzo Co., Ltd.) was used as an enzyme, and the PCR synthesis product was cloned into pT7blue. With regard to the original DNA, each DNA sequence on about 5 clones was determined. According to a series of these conversion reactions, cytosine was converted to uridine, and methylated cytosine was read as cytosine per se, thereby identifying the existence of a methyl group. The difference in nucleotide sequences was analyzed by DNASIS-Mac v3.7.

About 10 plants of chrysanthemum transformants obtained in Example 4 were analyzed. As a result, in a chrysanthemum transformant exhibiting high expression of the Gus gene, there were relatively few methylated cytosines in the 35S promoter, and methylation ratio in about 5 clones was also low. On the other hand, in the plants from which no expression of the Gus gene was detected, almost all the cytosines including CG and CNG in the 35S promoter were methylated at a high ratio. Here, as comparative experiment, with regard to tobacco (variety: Xanthi) having the same gene introduced thereinto, plants thereof exhibiting high expression of the Gus gene were investigated, and no methylated cytosine was detected. Incidentally, methylation degree of cytosine was investigated regarding a complementary DNA strand to the 35S promoter in chrysanthemum. Although there were scattered methylated cytosines, specific cytosines were not modified and there was no correlation with Gus gene expression. On the other hand, methylation of a structural gene was also investigated and cytosine modification was hardly observed at least from the translation initiation site (ATG) to nucleotide no. about 600, regardless of expression strength. The above relationship between cytosine methylation and expression level was observed not only in Gus gene but also in chrysanthemum having introduced thereinto a structure wherein a double-stranded RNA specific RNase gene (Nature Biotechnoloty, 15, 1290-1297 described before) was ligated downstream of the 35S promoter.

Next, methylation was investigated in the same manner concerning chrysanthemum having pKT81 introduced thereinto and exhibiting high expression of the Gus gene. As a result, by transformation, some plants were not subjected to methylation at all, and in the other plants cytosines at a site other than palindrome structure were strongly methylated from the promoter to the Gus gene. However, all groups of plants strongly expressed the Gus gene, and because of this, methylation of cytosine residues other than the palindrome structures (CG and CNG) was considered to exert a little influence on gene expression.

Accordingly, as one method for enhancing structural gene expression, it was considered important to convert nucleotide sequence having a palindrome structure of CG and CNG at the site of the promoter of the introduced gene. In passing, among palindrome structures, in the case of pKT83, though CG sequence (nos. 185 and 197 cytosine nucleotide in SEQ ID NO:2) in a short sequence, so-called ocs sequence has a sequence not to be converted, the effect of this site had a tendency to show higher activity than pKT81 according to the results of Example 3 (FIGS. 4 and 5). Thus, to prepare a high expression promoter, without conversion of the palindrome structure of this ocs sequence, it was indicated that much higher expression in vivo can be accomplished.

Example 6

Transformation of Carnation

For the purpose of increasing the expression level of an NPTII gene by a methylation-free promoter and enhancing selection efficiency with a marker, a Nos promoter of NPTII expression cassette was changed to the methylation-free promoter. To put it simply, the Nos promoter and the MF-48 promoter in the cassette were replaced with a DNA fragment between HindIII and XbaI, thereby preparing a cassette of MF-48 promoter, NPTII and Nos terminator. By replacing the NPTII expression cassette (HindIII to KpnI) in pKT-11 with the obtained cassette, pKT74 was prepared as a binary vector ligated to Gus expression cassette.

This pKT74 and, as a control, pKT11, were introduced into Agrobacterium tumefaciens LBA 4404 strains by electroporation, and these were inoculated on 3 ml of YEB-Km medium. After cultivation at 28° C. for 16 hours, strain cells were collected by centrifugation and suspended in 10 ml of the following infected medium, thereby preparing an infected solution. The compositions of the YEB-Km medium and the infected medium were as follows.

YEB-Km medium; 5 g/l beef extract, 1 g/l yeast extract, 5 g/l peptone, 5 g/l sucrose, 2 mM magnesium sulfate (pH 7.2), and 50 mg/l kanamycin Infected medium; inorganic salts and vitamins of 1/2 concentration of MS (Murashige & Skoog, Physiol. Plant., 15 (1962) 473-497), 15 g/l sucrose, 10 g/l glucose, and 10 mM MES (pH 5.4)

Leaf stems were cut off from sterile plants of carnation cultivar, Scania (Dianthus caryophyllus L), and they were dipped for 10 minutes into Agrobacterium infected solutions each having introduced thereinto pKT11 and pKT74. After wiping off any excess of the infected solution with a paper filter, they were transplanted in the following co-cultivation medium and cultivated at 25° C. in the dark. After three-day cultivation, they were transplanted in the following selection medium and cultivated for 3 weeks, thereby obtaining G418 resistant calli. The cultivation in the selection medium was conducted with the conditions of 16-hour lighting (light density 32 μE/m$^2$s)/8-hour non-lighting at 25° C.

Co-cultivation medium; inorganic salts and vitamins of MS medium, 30 g/l sucrose, 0.5 mg/l indolebutyric acid, 0.22 mg/l thidiazuron, 8 g/l agar, 5 mM MES (pH 5.8), and 100 mg/L acetosyringone.

Selection medium; inorganic salts and vitamins of MS medium, 30 g/l sucrose, 0.5 mg/l indolebutyric acid, 0.22 mg/l thidiazuron, 8 g/l agar, 5 mM MES (pH 5.8), 25 mg/l G418, and 300 mg/l cefotaxime

Example 7

Selection of Carnation Transformant

*Agrobacterium tumefaciens* LBA 4404 strains each containing pKT11 and pKT74 were transformed in accordance with the method of Example 6, and using the obtained G418 resistance seedlings, plants were regenerated in MS medium containing no plant growth regulating substances (indolebutyric acid, thidiazuron) but G418.

From the grown plants, plants containing an NPTII gene as a foreign gene were detected by conducting PCR, and it was confirmed that the thus-obtained redifferentiated plants were transformants. Here as a primer for specific amplification of an NPTII gene-specific sequence, the sequences of TAAAGCACGAGGAAGCGGT (SEQ ID NO:5) and GCACAACAGACAATCGGCT (SEQ ID NO:6) were used. The reaction conditiona for PCR were heating at 94° C. for 5 minutes; 30 cycles of 30 seconds at 94° C., 1 minute at 55° C., and 1 minute at 72° C.; followed by a reaction at 72° C. for 10 minutes. In this reaction, ExTaq polymelase (manufactured by Takara Shuzo Co., Ltd.) was used as an enzyme.

Plants from which the NPTII gene was detected by PCR were used as a transformant. With regard to each of pKT11 and pKT74, the transformation efficiency ratio was calculated as the number of transformants per leaf piece used. The ratio for pKT11 was 5% or less, and in contrast the ratio for pKT74 was 25% or more. Incidentally, Gus activity was determined in the same manner as in Example 3, and it was confirmed that all the recombinants expressed the Gus gene.

In view of the above results, it was considered that MF-48 promoter could act on expression of a selection marker gene with remarkable efficiency.

All publications, patents and patent applications cited herein are incorporated by reference in their entirety.

The invention claimed is:

1. An isolated DNA molecule comprising a polynucleotide having the sequence of SEQ ID NO: 1 from nucleotide No. 7 to nucleotide No. 272.

2. An isolated DNA molecule comprising a polynucleotide having the sequence of SEQ ID NO: 1.

3. A recombinant construct comprising the DNA according to claims 1 or 2.

4. The recombinant construct according to claim 3, comprising a structural gene DNA and the DNA according to claims 1 or 2 which is incorporated at the 5' site of the structural gene DNA in a manner such that it is expressed.

5. The recombinant construct according to claim 3, further comprising a selection marker gene DNA and the DNA according to claims 1 or 2 which is incorporated at the 5' site of the selection marker gene DNA in a manner such that a selection marker gene is expressed.

6. A method for selecting a transformant host, where the method comprises the steps of:
   transforming a host with the recombinant construct of claim 5;
   culturing the obtained host and determining whether or not the host expresses the selection marker gene; and
   selecting a host expresses the selection marker gene,
   wherein the host is a plant cell.

* * * * *

SEQUENCE LISTING

```
<160> NUMBER OF SEQ ID NOS: 24

<210> SEQ ID NO 1
<211> LENGTH: 320
<212> TYPE: DNA
<213> ORGANISM: Artificial Sequence
<220> FEATURE:
<223> OTHER INFORMATION: Description of Artificial Sequence:Synthetic
      DNA comprising promotor sequence

<400> SEQUENCE: 1
aagcttaaaa ggaaggtggc tcctacaaat gccatcattg tgataaagga aaggctatca      60
ttgaagatgc ctctacctat agtggtccca aagatggacc cccacccatg aggagcatgg     120
tagaaaaaga agatgttcca accatgtctt caaagcaagt ggattgatgt ggatcctcca     180
atgatgtcaa ggatgatgtc aaatcccact atccttgcca agatcttccc tctatataag     240
gaagttcatt tcatttggag aggacaaggt actctagact tctttcctca accttctttc     300
ttcttatata tcataccatg                                                  320

<210> SEQ ID NO 2
<211> LENGTH: 320
<212> TYPE: DNA
<213> ORGANISM: Artificial Sequence
<220> FEATURE:
<223> OTHER INFORMATION: Description of Artificial Sequence:Synthetic
      DNA comprising promotor sequence

<400> SEQUENCE: 2
aagcttaaaa ggaaggtggc tcctacaaat gccatcattg tgataaagga aaggctatca      60
ttgaagatgc ctctacctat agtggtccca aagatggacc cccacccatg aggagcatgg     120
tagaaaaaga agatgttcca accatgtctt caaagcaagt ggattgatgt ggatcctcca     180
atgacgtcaa ggatgacgtc aaatcccact atccttgcca agatcttccc tctatataag     240
gaagttcatt tcatttggag aggacaaggt actctagact tctttcctca accttctttc     300
ttcttatata tcataccatg                                                  320

<210> SEQ ID NO 3
<211> LENGTH: 370
<212> TYPE: DNA
<213> ORGANISM: Artificial Sequence
```

```
<220> FEATURE:
<223> OTHER INFORMATION: Description of Artificial Sequence:Synthetic
      DNA comprising promotor sequence

<400> SEQUENCE: 3
aagcttaaaa ggaaggtggc tcctacaaat gccatcattg tgataaagga aaggctatca    60
ttgaagatgc ctctacctat agtggtccca aagatggacc cccacccatg aggagcatgg   120
tagaaaaaga agatgttcca accatgtctt caaagcaagt ggattgatgt ggatcctcca   180
atgatgtcaa ggatgatgtc aaatcccact atccttgcca agatcctcca atgatgtcaa   240
ggatgatgtc aaatcccact atccttgcca agatcttccc tctatataag gaagttcatt   300
tcatttggag aggacaaggt actctagact tctttcctca accttctttc ttcttatata   360
tcataccatg                                                           370

<210> SEQ ID NO 4
<211> LENGTH: 470
<212> TYPE: DNA
<213> ORGANISM: Artificial Sequence
<220> FEATURE:
<223> OTHER INFORMATION: Description of Artificial Sequence:Synthetic
      DNA comprising promotor sequence

<400> SEQUENCE: 4
aagcttaaaa ggaaggtggc tcctacaaat gccatcattg tgataaagga aaggctatca    60
ttgaagatgc ctctacctat agtggtccca aagatggacc cccacccatg aggagcatgg   120
tagaaaaaga agatgttcca accatgtctt caaagcaagt ggattgatgt ggatcctcca   180
atgatgtcaa ggatgatgtc aaatcccact atccttgcca agatcctcca atgatgtcaa   240
ggatgatgtc aaatcccact atccttgcca agatcctcca atgatgtcaa ggatgatgtc   300
aaatcccact atccttgcca agatcctcca atgatgtcaa ggatgatgtc aaatcccact   360
atccttgcca agatcttccc tctatataag gaagttcatt tcatttggag aggacaaggt   420
actctagact tctttcctca accttctttc ttcttatata tcataccatg               470

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 5
taaagcacga ggaagcggt                                                 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 6
gcacaacaga caatcggct                                                 19

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:Primer
```

-continued

<400> SEQUENCE: 7
gaatgttaat ttatagatgg ttagagaggt ttatgtagta gg                    42

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 8
ccatattctc tccaaataaa ataaac                                      26

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 9
agtaataatt ttaggaaatt aaatattttt ttaagaagg                        39

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 10
tattctctcc aaataaaata aacttc                                      26

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 11
ctattccaat ataaacaatt caaaacttac                                  30

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 12
tgaaatgaat tttttatat agaggaaggg ttttgtg                           37

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 13
caacataata aaacacaaca cacttatcta c                                31

<210> SEQ ID NO 14
<211> LENGTH: 36

```
<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 14
atgaattttt ttatatagag gaagggtttt gtgaag                                 36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 15
gaagaaattt ttgttaatat ggtggagtat gatatg                                 36

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence:Primer

<400> SEQUENCE: 16
ccaatcaaca aacacataat tacaatctta cacaacatac atc                         43

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 17
gggatgatgt ataattttat tattttttgt aaga                                   34

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:Primer

<400> SEQUENCE: 18
cataacatca acttcaaata acatataacc accctaatac                             40

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 19
cttcaataac aaattcattt taacaatcat acc                                    33

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 20
```

```
acaaattcat tttaacaatc ataccttaac t                                           31

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence:Primer

<400> SEQUENCE: 21
gaggatttaa aaggaaggtg gttttttataa atgttattat tg                              42

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 22
ccacaatttt cacaatccaa actaaatacc cacaaacc                                    38

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence:Primer

<400> SEQUENCE: 23
ggatttaaaa ggaaggtggt ttttataaat gttattattg tg                               42

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 24
caattttcac aatccaaact aaatacccac aaaccatc                                    38
```